(12) United States Patent
Freese et al.

(10) Patent No.: US 9,915,611 B2
(45) Date of Patent: Mar. 13, 2018

(54) OPTICAL COMPUTING DEVICE AND METHOD FOR COMPENSATING LIGHT FLUCTUATIONS

(71) Applicant: Halliburton Energy Services, Inc., Houston, TX (US)

(72) Inventors: Robert P. Freese, Houston, TX (US); David L. Perkins, The Woodlands, TX (US); William J. Soltmann, The Woodlands, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 14/909,794

(22) PCT Filed: Oct. 10, 2013

(86) PCT No.: PCT/US2013/064298
§ 371 (c)(1),
(2) Date: Feb. 3, 2016

(87) PCT Pub. No.: WO2015/053776
PCT Pub. Date: Apr. 16, 2015

(65) Prior Publication Data
US 2016/0202181 A1    Jul. 14, 2016

(51) Int. Cl.
*G01N 21/00* (2006.01)
*G01N 21/59* (2006.01)
*G01N 21/31* (2006.01)

(52) U.S. Cl.
CPC ............. *G01N 21/59* (2013.01); *G01N 21/31* (2013.01)

(58) Field of Classification Search
CPC .... G01N 21/534; G01N 21/59; G01N 21/255; G01J 3/42; G01J 1/16
(Continued)

(56) References Cited

U.S. PATENT DOCUMENTS 5,977,546 A * 11/1999 Carlson ................ G01N 21/031
250/339.13
6,163,395 A    12/2000 Nemecek et al.
(Continued)

FOREIGN PATENT DOCUMENTS

| IE | 990865 A2 | 11/2011 |
|---|---|---|
| WO | WO 2008/057912 A2 | 5/2008 |
| WO | WO 2008/121693 A1 | 10/2008 |

OTHER PUBLICATIONS

Beloborodov, et al., "Method of Spectral Compensation Like an Effective Tool to Reduce an Effect of Interfering Components on the Measurement of CO2, CH4, CO, and SO2 in Atmosphere," D.I. Mendeleyev Institute for Metrology, St. Petersburg, Russia.
(Continued)

*Primary Examiner* — Tarifur Chowdhury
*Assistant Examiner* — Md M Rahman
(74) *Attorney, Agent, or Firm* — Haynes and Boone, LLP

(57) ABSTRACT

An optical computing device adapted to compensate for the effects of light intensity fluctuation through the use of optical elements that generate a normalization optical channel (or B Channel) having a light intensity that is substantially equal to the light intensity of the characteristic optical channel (or A Channel). As a result, highly accurate normalizations are obtained which give rise to the most accurate results from the optical computing device.

25 Claims, 4 Drawing Sheets

(58) Field of Classification Search
USPC .......................................................... 356/434
See application file for complete search history.

(56) References Cited

U.S. PATENT DOCUMENTS

| | | | |
|---|---|---|---|
| 6,583,866 B2 | 6/2003 | Jung et al. | |
| 6,888,633 B2 | 5/2005 | Vander Jagt et al. | |
| 7,245,373 B2 | 7/2007 | Soller et al. | |
| 7,719,680 B2 * | 5/2010 | Christian | G01J 3/02 356/319 |
| 7,923,801 B2 | 4/2011 | Tian et al. | |
| 7,944,557 B2 | 5/2011 | Hagler | |
| 8,358,418 B2 * | 1/2013 | Myrick | G01N 21/9508 356/301 |
| 2002/0154315 A1 | 10/2002 | Myrick | |
| 2008/0316484 A1 * | 12/2008 | Christian | G01J 3/02 356/326 |
| 2011/0299070 A1 | 12/2011 | Christiansen et al. | |
| 2013/0032334 A1 | 2/2013 | Freese et al. | |

OTHER PUBLICATIONS

Haibach, et al., "Precision in Multivariate Optical Computing," Applied Optics, 2004, vol. 43, pp. 2130-2140.

International Search Report and The Written Opinion of the International Searching Authority, or the Declaration, dated Mar. 11, 2014, PCT/US2013/064298, 10 pages, ISA/US.

Myrick, et al., "A Single-Element All-Optical Approach to Chemometric Prediction,", Vibrational Spectroscopy, 2002, vol. 28, pp. 73-81.

Nelson, et al., "Multivariate Optical Computation for Predictive Spectroscopy," Anal. Chem., 1998, vol. 70, pp. 73-82.

Priore, et al., "Miniature Stereo Spectral Imaging System for Multivariate Optical Computing," Appl. Spectrosc., 2004, vol. 58, pp. 870-873.

Profeta, et al. "Spectral Resolution in Multivariate Optical Computing," Spectrochim. Acta A Mol. Biomol. Spectrosc., 2007, vol. 67, No. 207, pp. 483-502.

Roy, et al., "Neutralized Drift Compression Experiments with a High-Intensity Ion Beam," Nuclear Instruments and Methods in Physics Research, Section A, Feb. 2007, vol. 577, pp. 233-230.

Simcock, et al., "Precision in Imaging Multivariate Optical Computing," Applied Optics, 2007, vol. 46, pp. 1066-1080.

Soyemi, et al. "Design and Testing of a Multivariate Optical Element (MOE): The First Demonstration of Multivariate Optica Computing for Predictive Spectroscopy," Anal. Chem. 2001, vol. 73, pp. 1069-1079.

Soyemi, et al., "Design of Angle-Tolerant Multivariate Optical Elements for Chemical Imaging," Applied Optics, 2002, vol. 41, pp. 1936-1941.

European Search Report issued for European Application No. 13895437 dated Feb. 8, 2017, 6 pages.

* cited by examiner

OPTICAL COMPUTING DEVICE AND METHOD FOR COMPENSATING LIGHT FLUCTUATIONS

The present application is a U.S. National Stage patent application of International Patent Application No. PCT/US2013/064298, filed on Oct. 10, 2013, the benefit of which is claimed and the disclosure of which is incorporated herein by reference in its entirety.

FIELD OF THE INVENTION

The present invention relates generally to optical systems and, more specifically, to an optical computing device adapted to compensate for the effects of light intensity fluctuations.

BACKGROUND

In recent years, optical computing techniques have been developed for applications in the Oil and Gas Industry in the form of optical sensors on downhole or surface equipment to evaluate a variety of fluid properties. An optical computing device is a device configured to receive an input of electromagnetic radiation from a substance or sample of the substance and produce an output of electromagnetic radiation from a processing element, also referred to as an optical element. The optical element may be, for example, a narrow band optical filter or an Integrated Computational Element ("ICE") (also known as a Multivariate Optical Element ("MOE").

Fundamentally, optical computing devices utilize optical elements to perform calculations, as opposed to the hardwired circuits of conventional electronic processors. When light from a light source interacts with a substance, unique physical and chemical information about the substance is encoded in the electromagnetic radiation that is reflected from, transmitted through, or radiated from the sample. Thus, the optical computing device, through use of the optical element and one or more detectors, is capable of extracting the information of one or multiple characteristics/properties or analytes within a substance and converting that information into a detectable output signal reflecting the overall properties of a sample.

The characteristic or analyte of interest is directly related to the intensity of the light transmitted both through the sample and through the ICE. This light is generally referred to as the "A" Channel. One challenge in optical computing or ICE computing devices is that the light intensity in the A Channel may fluctuate. Such fluctuations might occur for a variety of reasons, including weakening of the bulb over time, in response to analyte concentration variations, or other spurious effects such as dust and dirt accumulation on the optical elements and windows. These spurious effects will cause the A Channel light intensity to be incorrect and, therefore, introduce negative factors into the accuracy of the optical device.

Conventional methods to provide sufficient solutions to the light fluctuation problem normalize or ratio out the spurious effects using a second "B" Channel. Thus, if the intensity of the light source were to be halved, then the assumption has been that the A Channel intensity would also be halved (thus creating an error), and the B Channel would be halved as well; thus, the A/B ratio remains the same. However, through our work in this area, it has been discovered that this assumption is incorrect. In other words, the light A/B ratio does not remain the same. Rather, it is now understood that when the light source intensity is halved, the A/B ratio does not remain the same and, thus, an error is introduced using conventional methods. This is especially troubling given that optical computing devices often have very low sensitivities, and even a one percent error in the A/B ratio could result in an error factor of 2, 3 or even 10 in the measured concentration value.

Accordingly, there is a need in the art for an optical computing device and method that overcomes the shortcomings of conventional normalization techniques to combat the effects of light fluctuation, thus providing a more reliable and accurate optical computing device.

DESCRIPTION OF ILLUSTRATIVE EMBODIMENTS

Figure 1:
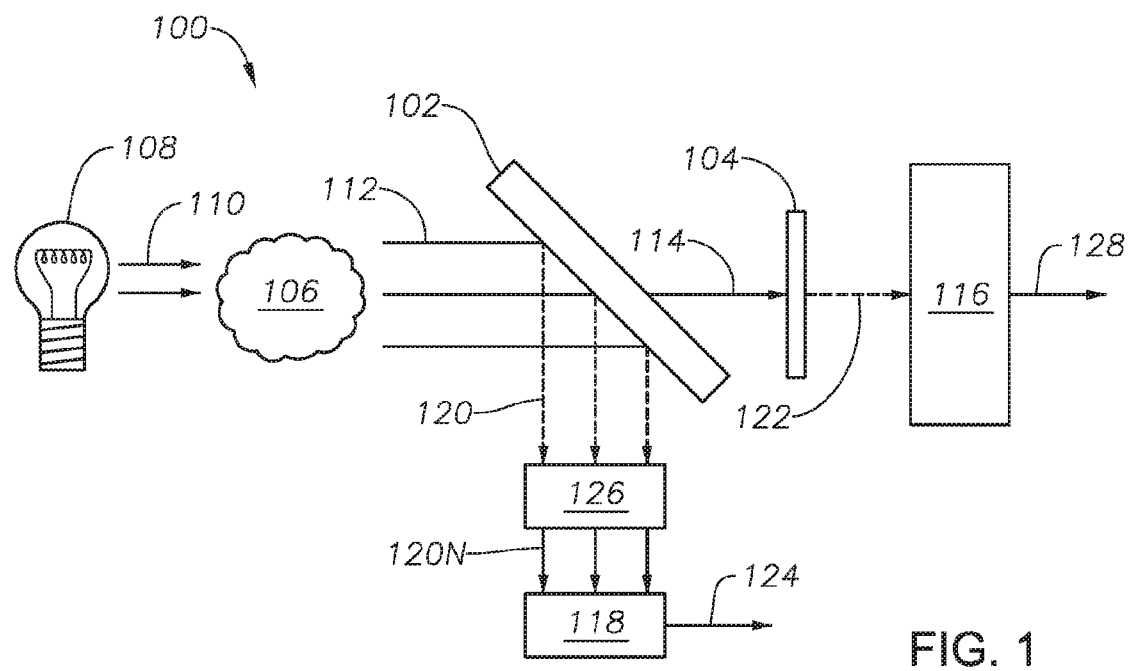
FIG. 1 is a block diagrammatical illustration of an optical computing device utilizing a normalization optical channel according to certain exemplary embodiments of the present invention.

Illustrative embodiments and related methodologies of the present invention are described below as they might be employed in a device and method to compensate for light fluctuation in an optical computing device. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the invention will become apparent from consideration of the following description and drawings.

As described herein, exemplary embodiments of the present invention are directed to compensation methods that minimize the effects of light source fluctuation in optical computing devices. As described herein, certain embodiments of the present invention compensate for the effects of light intensity fluctuations in an optical device by generating a normalization optical channel, or B Channel, having an integrated light intensity that is equal or substantially equal to the integrated light intensity of the characteristic optical channel, or A Channel. As understood in the art, the intensity of an optical element is wavelength dependent, and, in certain embodiments, all wavelengths may be measured at once (integrated) using a single detector. Thus, in such embodiments, the detector voltage will be the integrated intensity over all wavelengths. Accordingly, transmission value and light intensity refers to the integrated transmission light intensity as measured by an optical transducer.

To achieve the foregoing objective in a first exemplary embodiment, the B Channel comprises a neutral density element whose transmission value is substantially equal to the transmission value of the optical element utilized in the A Channel. Alternatively, the B Channel may utilize an aperture whose physical dimensions are designed to generate a light intensity substantially equal to that of the A Channel. In a second exemplary embodiment, the B Channel may utilize a "virtual" optical element comprised of at least two optical elements whose outputs are combined to generate a light intensity substantially equal to that of the A Channel. Therefore, fluctuations in the light intensity can be compensated for independently of the chemical changes within the material being measured, thus dramatically increasing the accuracy of the computing device.

As will be described in more detail below, each optical computing device described herein optically interacts with a sample of interest (wellbore fluid, for example) to determine a characteristic of the sample. In certain exemplary embodiments, the characteristics determined include the presence and quantity of specific inorganic gases such as, for example, $CO_2$ and $H_2S$, organic gases such as methane (C1), ethane (C2) and propane (C3), saline water, dissolved ions (Ba, Cl, Na, Fe, or Sr, for example), or various other characteristics (pH, density and specific gravity, viscosity, total dissolved solids, sand content, etc.). In certain embodiments, a single optical computing device may detect a single characteristic or multiple characteristics, as will be understood by those ordinarily skilled in the art having the benefit of this disclosure.

FIG. 1 is a block diagram illustrating an optical computing device 100, in transmission mode, adapted to compensate for the effects of light intensity fluctuations according to certain exemplary embodiments of the present invention. As shown in FIG. 1, an electromagnetic radiation source 108 may be configured to emit or otherwise generate electromagnetic radiation 110. As understood in the art, electromagnetic radiation source 108 may be any device capable of emitting or generating electromagnetic radiation. For example, electromagnetic radiation source 108 may be a light bulb, UV light, vacuum UV light, light emitting device, laser, blackbody emitted from sample 106, photonic crystal, or X-Ray source, etc. In one embodiment, electromagnetic radiation 110 may be configured to optically interact with the sample 106 and generate sample-interacted light 112 directed to a beam splitter 102. Sample 106 may be any fluid, solid substance or material such as, for example, rock formations, concrete, other solid surfaces, etc. While FIG. 1 shows electromagnetic radiation 110 passing through or incident upon sample 106 to produce sample-interacted light 112 (i.e., transmission mode or fluorescent mode), it is also contemplated herein to reflect electromagnetic radiation 110 off of sample 106 (i.e., reflectance mode), such as in the case of a sample 106 that is translucent, opaque, or solid, and equally generate the sample-interacted light 112.

Sample 106 may be provided to device 100 through a flow pipe or sample cell, for example, containing sample 106, whereby it is introduced to electromagnetic radiation 110. After being illuminated with electromagnetic radiation 110, sample 106 containing an analyte of interest (a characteristic of the sample, for example) produces an output of electromagnetic radiation (sample-interacted light 112, for example). Although not specifically shown, one or more spectral elements may be employed in device 100 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation. Various other configurations and applications of spectral elements that may be employed with the present invention, as will be understood by those ordinarily skilled in the art having the benefit of this disclosure.

Still referring to the exemplary embodiment of FIG. 1, beam splitter 102 is employed to split sample-interacted light 112 into a transmitted electromagnetic radiation 114 (A Channel or characteristic optical channel) having a given light intensity and a reflected electromagnetic radiation 120 (B Channel or normalization optical channel), also having a given light intensity. Transmitted electromagnetic radiation 114 is then directed to one or more optical elements 104. Optical element 104 may be a variety of optical elements such as, for example, one or more narrow band optical filters or ICEs arranged or otherwise used in series in order to determine the characteristics of sample 106. In those embodiments using ICEs, the ICE may be configured to be associated with a particular characteristic of sample 106 or may be designed to approximate or mimic the regression vector of the characteristic in a desired manner, as would be understood by those ordinarily skilled in the art having the benefit of this disclosure. Additionally, in an alternative embodiment, optical element 104 may function as both a beam splitter and computational processor, as will be understood by those same ordinarily skilled persons.

Nevertheless, transmitted electromagnetic radiation 114 then optically interacts with optical element 104 to produce optically interacted light 122. In this embodiment, optically interacted light 122, which is related to the characteristic or analyte of interest, is conveyed to detector 116 for analysis and quantification. Detector 116 may be any device capable of detecting electromagnetic radiation, and may be generally characterized as an optical transducer. For example, detector 116 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, and/or combinations thereof, or the like, or other detectors known to those ordinarily skilled in the art. Each element in detector 116 is further configured to produce an output signal 128 in the form of a voltage that corresponds to the particular characteristic of the sample 106. In at least one embodiment, output signal 128 produced by detector 116 and the concentration of the characteristic of the sample 106 may be directly proportional. In other embodiments, the relationship may be a polynomial function, an exponential function, and/or a logarithmic function.

Optical computing device 100 also includes a second detector 118 arranged to receive and detect reflected electromagnetic radiation of the normalization optical channel and output a compensating signal 124. As understood in the art, reflected electromagnetic radiation 120 may include a variety of radiating deviations stemming from electromagnetic radiation source 108 such as, for example, intensity fluctuations in the electromagnetic radiation, interferent fluctuations (for example, dust or other interferents passing in front of the electromagnetic radiation source), combinations thereof, or the like. Thus, second detector 118 detects such radiating deviations as well. In an alternative embodiment, second detector 118 may be arranged to receive a portion of the sample-interacted light 112 instead of reflected electromagnetic radiation 120, and thereby compensate for electromagnetic radiating deviations stemming from the electromagnetic radiation source 108. In yet other embodiments, second detector 118 may be arranged to receive a portion of electromagnetic radiation 110 instead of reflected electromagnetic radiation 120, and thereby likewise compensate for electromagnetic radiating deviations stemming from the electromagnetic radiation source 108. Moreover, a single detector may be utilized in place of detectors 116,118. Those ordinarily skilled in the art having the benefit of this disclosure will realize there are a variety of design alterations which may be utilized in conjunction with the present invention.

Although not shown in FIG. 1, in certain exemplary embodiments, detector 116 and second detector 118 may be communicably coupled to a signal processor (not shown) such that compensating signal 124 indicative of electromagnetic radiating deviations may be provided or otherwise conveyed thereto. The signal processor may then be configured to computationally combine compensating signal 124 with output signal 128 to provide a more accurate determination of the characteristic of sample 106. However, in other embodiments that utilized only one detector, the signal processor would be coupled to the one detector. Nevertheless, in the embodiment of FIG. 1, for example, the signal processor computationally combines compensating signal 124 with output signal 128 via multivariate statistical analysis techniques such as, for example, standard partial least squares which are available in most statistical analysis software packages (for example, XL Stat for MICROSOFT® EXCEL® the UNSCRAMBLER® from CAMO Software and MATLAB® from MATHWORKS®), as will be understood by those ordinarily skilled in the art having the benefit of this disclosure.

As previously described, optical computing device 100 may undergo fluctuations in light intensity which may skew the A/B signal ratios, thus resulting in output errors. To combat this phenomenon, optical computing device 100 is adapted to generate a normalization optical channel whose light intensity is substantially equal to the light intensity of the characteristic optical channel. To do so, a first exemplary embodiment of optical computing device 100 includes a neutral density element 126 positioned to interact with reflected electromagnetic radiation 120. As understood in the art, a neutral density element may be, for example, an optical element that equally weights all wavelengths at a certain value. As a result, regardless of the intensity of reflected electromagnetic radiation 120, neutral density element 126 will output a light having a flat, or normalized, profile. Neutral density element 126 is selected to have integrated transmittance values which are substantially equal to those of optical element 104. As a result, the light output by neutral density element 126 will have an intensity that is substantially equal or equal in magnitude to optically interacted light 122. In certain exemplary embodiments, "substantially equal" light intensities described herein are, for example, those wherein the resulting A/B Channel intensity ratio is 2:1, 1:2, 1.2:1, 1:1.2, 1.1:1, 1:1.1, less than 1.05:1, or 1:1.05. Those ordinarily skilled in the art having the benefit of this disclosure will realize that the transmittance properties of optical elements may be specifically combined and tailored to achieve any number of desired ratios as described herein.

Alternatively, an aperture may be utilized as the optical element in place of neutral density element 126. In such an alternate embodiment, the physical dimensions of the aperture would be selected to generate the normalization optical channel having a light intensity equal to that of the characteristic optical channel. For example, if the optical channel consisted of a planar wave with uniform intensity distribution in a 1" optical diameter beam, then insertion of an optical aperture less of less than 1" would reduce the intensity of the B channel by the square ratio of the aperture diameter to the nominal 1" beam diameter and thereby employed to make the A/B ratio essentially one. A half inch aperture, for example, would reduce the B intensity by a factor of 4. The planar wave example is one such implementation, but it is understood by those ordinarily skilled persons mentioned herein that virtually any beam profile can be employed and reduced via an aperture stop to achieve an A/B ratio of essentially 1.

During operation of optical computing device 100, the intensity of electromagnetic radiation 110 or sample-interacted light 112 may fluctuate due to, for example, wear of source 108, periodic electrical surges emanating from the voltage source (not shown) of electromagnetic source 108 or the physical characteristics of sample 106 (absorption, for example), or any other ambient interferent in the optical path. As a result, the ratio of the output signal 128 and compensating signal 124 will be skewed accordingly, thus resulting in output errors. To compensate for this, neutral density element 126, or an aperture, essentially filters reflected electromagnetic radiation 120 by equally weighing the wavelengths to output a normalized reflected electromagnetic radiation 120N of the normalization optical channel. In this exemplary embodiment, since neutral density element 126 was selected to match or closely approximate the transmittance properties of optical element 104, normalized reflected electromagnetic radiation 120N is of a magnitude identical or similar to the magnitude of optically interacted light 122. As a result, the output signal ratio (A/B channel) is flat or within 10% or less of the desired 1/1 total output signal ratio, thus resulting in accurate measurements. Accordingly, the effects of the light fluctuations have been compensated. Thereafter, the processor (not shown) coupled to detectors 116,118 may further processes the total output signal to determine the desired characteristics of sample 106.

Figure 2:
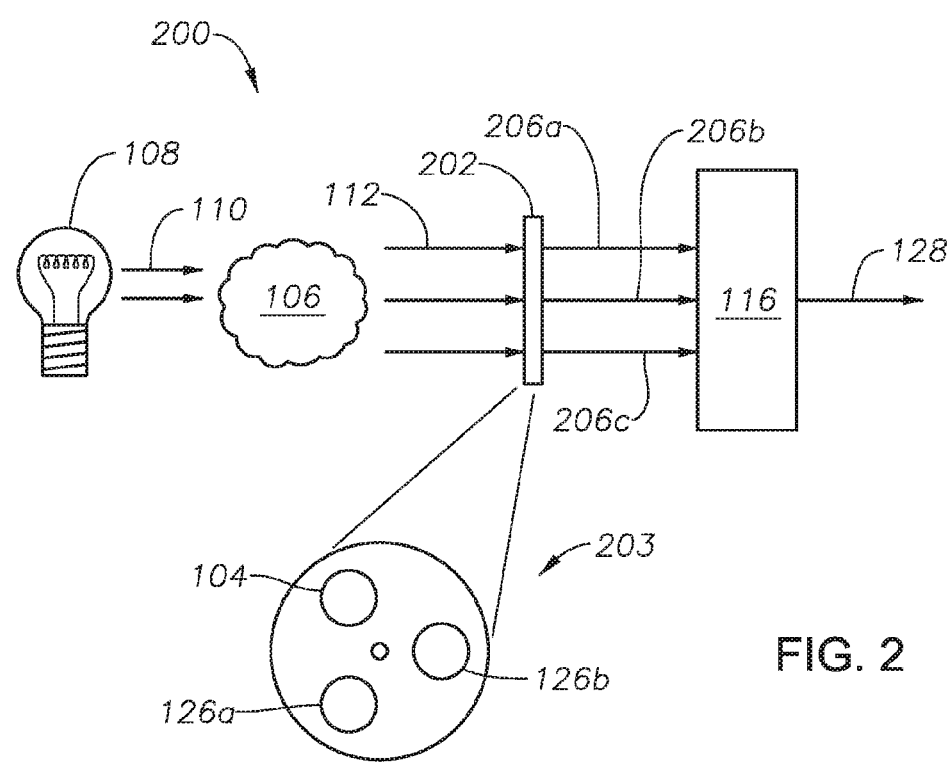
FIG. 2 is a block diagrammatical illustration of an optical computing device utilizing an alternative normalization optical channel according to certain exemplary embodiments of the present invention.

FIG. 2 illustrates yet another optical computing device 200, in the time domain, according to certain exemplary embodiments of the present invention whereby two or more optical elements are combined to create a virtual optical element that compensates for light fluctuations. Optical computing device 200 is somewhat similar to optical computing device 100 described with reference to FIG. 1 and, therefore, may be best understood with reference thereto, where like numerals indicate like elements. The device 200 may include a movable assembly 202 having at least one first optical element 104 and two or more second optical elements 126a and 126b associated therewith. As illustrated, the movable assembly 202 may be characterized at least in one embodiment as a rotating disc 203, such as, for example, a filter wheel, wherein first optical element 104 and second optical elements 126a,b are radially disposed for rotation therewith. FIG. 2 also illustrates corresponding frontal views of the moveable assembly 202, which is described in more detail below.

Those ordinarily skilled in the art having the benefit of this disclosure will readily recognize, however, that movable assembly 202 may be characterized as any type of movable assembly configured to sequentially align at least one detector with optically interacted light and/or one or more optical elements. Each first optical element 104 and second optical elements 126a,b may be similar in construction to those as previously described herein, and configured to be either associated or disassociated with a particular characteristic of the sample 106.

In certain exemplary embodiments, rotating disc 203 may be rotated at a frequency of about 0.1 RPM to about 30,000 RPM. In operation, rotating disc 203 may rotate such that the individual first optical element 104 and second optical elements 126a,b may each be exposed to or otherwise optically interact with the sample-interacted light 112 for a distinct brief period of time. Upon optically interacting with the sample-interacted light 112, first optical element 104 is configured to generate a characteristic optical channel that includes optically interacted light 206a (a first beam, for example) having a given light intensity. In addition, second optical elements 126a,b are configured to combinatorily generate a normalization optical channel that includes a first normalized electromagnetic radiation 206b (a second normalized beam, for example) and second normalized electromagnetic radiation 206c (a third normalized beam, for example), which combinatorily result in a virtual optical filter. In certain exemplary embodiments, the virtual optical element generates the necessary light intensity in real-time or via a look-up table. Nevertheless, detector 116 then receives each beam 206a-c and thereby generates a first output signal of the characteristic optical channel, and a second and third output signal of the normalization optical channel, respectively (output signal 128 comprises the first, second and third signals). Accordingly, a signal processor (not shown) communicatively coupled to detector 116 utilizes output signal 128 to computationally determine the sample characteristics.

Still referring to the exemplary embodiment of FIG. 2, second optical elements 126a,b may be a combination of one or more apertures and neutral density elements as previously described herein. Alternatively, second optical elements 126a,b may be one or more apertures and dispersive elements such as, for example, gratings, holographic optical elements, phase elements, etc., as will be understood by those ordinarily skilled in the art having the benefit of this disclosure. In yet another exemplary embodiment, the second optical elements 126a,b may comprise an optical element whose optical bandpass transmission function is not essentially spectrally flat with wavelength, as is typical for optical cut-on, cut-off, or bandpass filters. The transmission (or reflection or absorption) profile as a function of wavelength may, for example, be a linearly decreasing or increasing function with wavelength. In general, it is advantageous and a preferred embodiment to employ an element whose transmission profile has relatively few high frequency spikes and whose overall profile varies slowly, albeit arbitrarily, with wavelength, as these types of elements are more environmentally stable. However, it is understood by those ordinarily skilled persons mentioned herein that virtually any transmission profile or shape may be employed for optical elements 126a,b.

Moreover, in certain exemplary embodiments of FIG. 2, detector 116 may be configured to time multiplex beams 206a-c between the individually-detected beams. For example, optical element 104 may be configured to direct first beam 206a toward the detector 116 at a first time T1, second optical element 126a may be configured to direct second beam 206b toward the detector 116 at a second time T2, and second optical element 126b may be configured to direct third beam 206c toward detector 116 at a third time T3. Consequently, detector 116 receives at least three distinct beams of optically-interacted light which may be computationally combined by a signal processor (not shown) coupled to detector 116 in order to provide an output in the form of a voltage that corresponds to the characteristic of the sample, as previously described. In certain alternate embodiments, beams 206a-c may be averaged over an appropriate time domain (for example, about 1 millisecond to about 1 hour) to more accurately determine the characteristic of sample 106.

Accordingly, when the intensity of electromagnetic radiation 110 or sample-interacted light 112 begins to fluctuate, second optical elements 126a,b interact with the fluctuating wavelengths, equally weighing each, to produce a flat output signal, thus normalizing second beam 206b and third beam 206c. Thereafter, as previously described, detector 116 is positioned to detect first, second and third beams 206a-c in order to produce output signal 128. In either embodiment, a signal processor (not shown) may be communicably coupled to detector 128 such that output signal 128 may be processed as desired to computationally determine one or more characteristics of sample 106. Through use of second optical elements 126a,b, the processor then calculates the virtual neutral density in order to ensure the proper A/B output ratio is maintained, thus compensating for any light fluctuations to maintain the integrity of the measurements.

Figure 3:
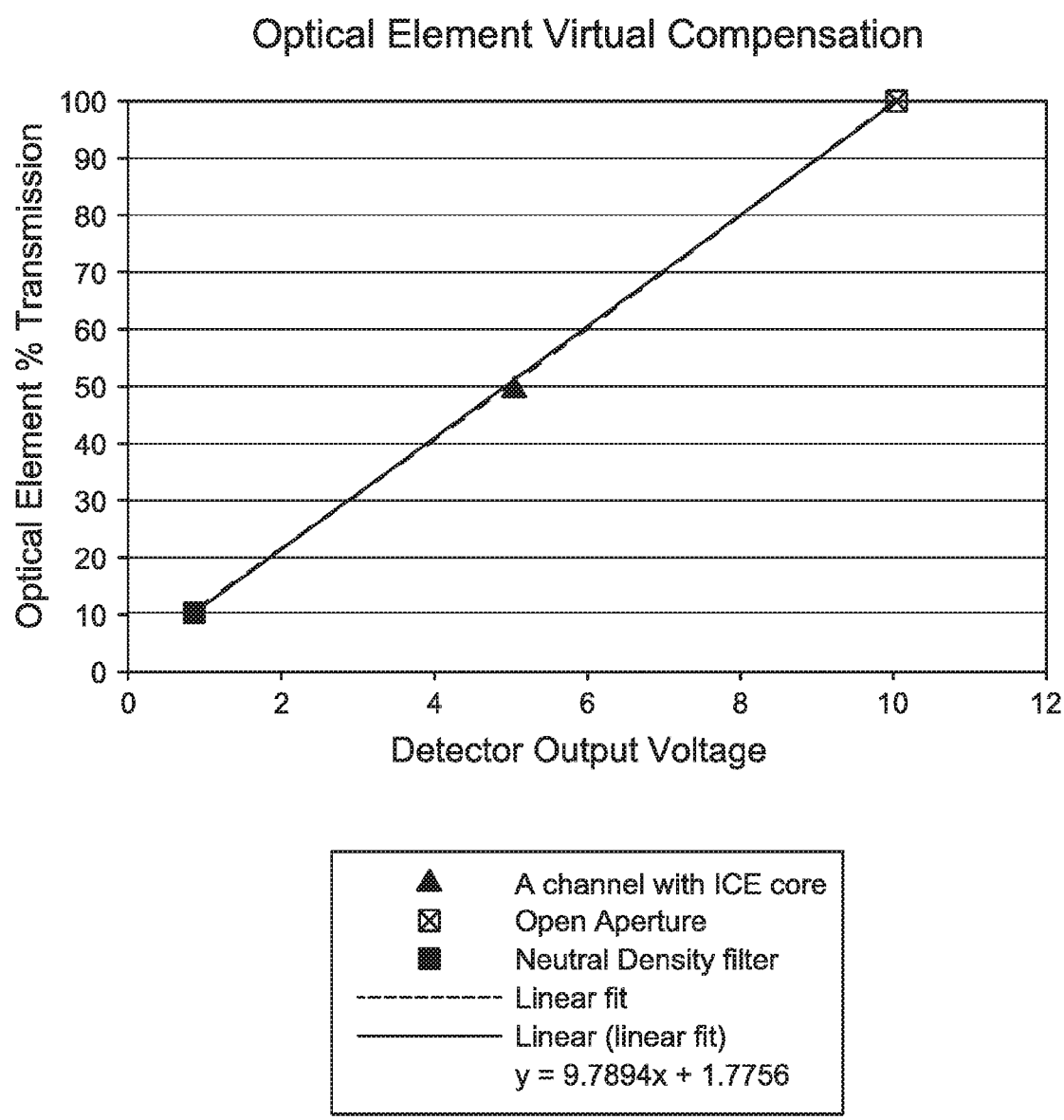
FIGS. 3-5 are graphs illustrating operation of a "virtual" optical element utilized in the optical computing device of FIG. 2, according to certain exemplary embodiments of the present invention.

FIG. 3 is a graph useful in illustrating the operation of a virtual optical element utilized in optical computing device 200, according to certain exemplary embodiments of the present invention. In the plotted example, Channel A (characteristic optical channel) utilizes an ICE at first optical element 104, while Channel B (normalization optical channel) utilizes an aperture and neutral density element as the second optical elements 126a,b. The percent transmission of each optical element is plotted along the y axis, while the detector output voltage is plotted along the x axis. In the illustrated example, an A Channel of 5 volts was utilized, and a B Channel voltage of 5 volts is shown to be achieved by combining signals from a 100% open aperture and a 10% neutral density filter. A linear equation for B Channel=5 volts may be solved from the line drawn between the 100% aperture and the 10% neutral density element. In this specific example, the linear equation may be expressed as:

$$y=9.7894x+1.7756 \qquad \text{Eq. (1).}$$

Note that in FIG. 3, the two neutral density filters produce voltages which bracket the desired A value, with one neutral density element having a larger voltage and the other having a lower voltage than the desired A value. While this configuration illustrates one exemplary embodiment, other exemplary embodiments may employ optical elements whose relationship can be different that that illustrated in FIG. 3.

Figure 4:
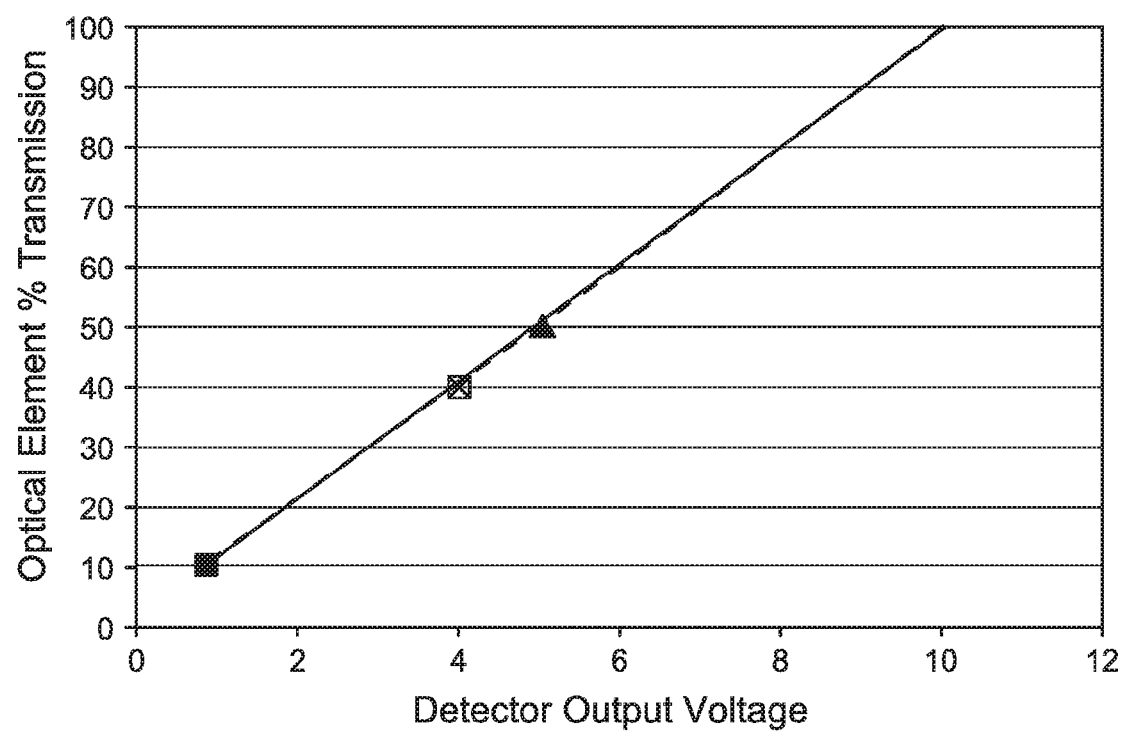

FIG. 4, for example, illustrates another graph corresponding to an exemplary optical computing device 200 in which two neutral density elements 126a,b are utilized. In this example, a B Channel voltage of 5 volts is found to be achieved with two neutral density elements 126a,b whose light intensities or transmissions are individually less than the desired A channel optical element 104. However, their light can be linearly combined using the Equation (1) to achieve a virtual B value substantially equal to that desired to match the A Channel.

Figure 5:
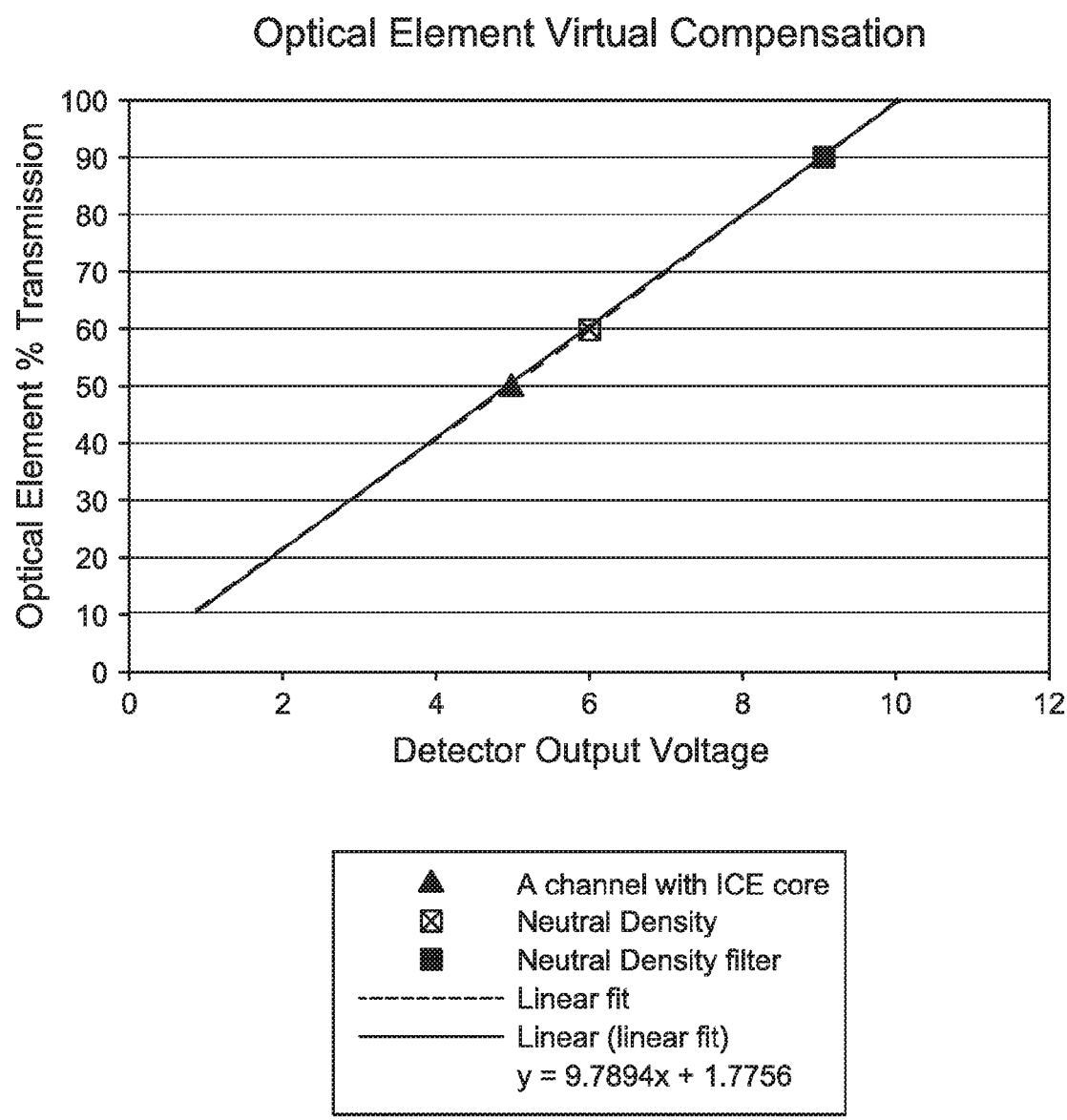

FIG. 5 illustrates yet another graph corresponding to an exemplary optical computing device 200 in which two neutral density elements 126a,b are utilized. Here, a B Channel voltage of 5 volts is found to be achieved with two neutral density elements 126a,b whose light intensities or transmission are individually more than the desired A channel optical element 104. However, again, their light intensities can be linearly combined using Equation (1) to achieve a virtual B value substantially equal to that desired to match the A channel. Accordingly, combinations of neutral density elements and/or apertures may be utilized to obtain a virtual B Channel signal that equals or substantially equals the A Channel, thereby obtaining a perfect or substantially perfect normalization and the most accurate results from the optical computing device. It is noted that, while the above examples in FIGS. 3-5 employ a linear combinatorial relationship to achieve the desired virtual B signal, in general, non-linear relationships (e.g., a quadratic, logarithmic, exponential, etc.) may also be employed as desired depending upon the specific optical elements employed. Furthermore, it is also noted that, while the examples in FIGS. 3-5 employ only two optical elements to achieve the virtual B channel, more than two elements can be employed in certain exemplary embodiments, especially those where the sensitivity is low and the virtual B value must be set extremely close to the A channel value.

In certain other exemplary embodiments, neutral density element 126a is selected to have a lower signal than optical element 104, while neutral density element 126b is selected to have a higher signal than that achieved with optical element 104. As a result, the virtual optical element is created between the values of neutral density elements 126a and 126b. As a result, the combined magnitude of the second normalized beam 206b and third normalized beam 206c is equal to or substantially equal to the magnitude of first beam 206a of optical element 104. Therefore, even during light fluctuations, beams 206a-c will maintain the correct output signal ratios, thus resulting in reliable and accurate measurements.

In yet other exemplary embodiments, second optical elements 126a,b utilized to generate the normalization optical channel comprise at least one optical element whose optical bandpass transmission function is not essentially spectrally flat with wavelength, as with typical optical cut-on, cut-off, or bandpass filters. The transmission (or reflection or absorption) profile as a function of wavelength may, for example, be a linearly decreasing or increasing function with wavelength. In general, it is advantageous and a preferred embodiment to employ an element whose transmission profile has relatively few high frequency spikes and whose overall profile varies slowly, albeit arbitrarily, with wavelength, as these types of elements are more environmentally stable. However, it is understood by those ordinarily skilled persons mentioned herein that virtually any transmission profile or shape may be employed for optical elements 126a,b.

In yet another alternate embodiment, various single or multiple ICEs may be positioned in series in a single optical computing device. Here, second optical elements 126a,b that generate the normalization optical channel are arranged in series relative to each other to thereby combinatorily generate the light of the normalized optical channel. In general, these elements may be placed anywhere on the carousel, and may be duplicated more than once on a given carousel. In some preferred embodiments, however, it is generally advantageous to place the optical elements adjacent to the ICEs of interest. These embodiments include applications where the sample interacted light is changing rapidly as compared to the transit time from each aperture on the carousel, as is the case when the properties of a moving sample may be changing rapidly when compared with the transit time from each aperture on the carousel.

Those ordinarily skilled in the art having the benefit of this disclosure will realize the aforementioned optical computing devices are exemplary in nature, and that there are a variety of other optical configurations which may be utilized. These optical configurations not only include the reflection, absorption or transmission methods described herein, but can also involve scattering (Raleigh & Raman, for example) as well as emission (fluorescence, X-ray excitation, etc., for example). In addition, the optical computing device may comprise a parallel processing configuration whereby the sample-interacted light is split into multiple beams. The multiple beams may then simultaneously go through corresponding ICE elements, whereby multiple analytes of interest are simultaneously detected. In other embodiments, the ICE may utilize two substantially different light sources (UV and IR, for example) to cover the optical activity of all the analytes of interest (i.e., some analytes might be only UV active, while others are IR active). Finally, it is noted that, while some of the above examples describe a neutral density element to achieve the B channel, many other optical elements may be used including various apertures, diffractive elements, gratings, HOE's (Holographic Optical Elements), and the like, and combinations thereof. Nevertheless, those ordinarily skilled in the art having the benefit of this disclosure will realize the choice of a specific optical configuration is mainly dependent upon the specific application and analytes of interest.

Accordingly, the present invention provides a solution to light fluctuation in computing devices that unexpectantly increases the accuracy of the output signal by a factor of 10 or more. As a result, foregoing advantages make the optical computing devices, and their variations described herein, particularly well-suited for field and downhole use.

Embodiments described herein further relate to any one or more of the following paragraphs:

1. An optical computing device, comprising electromagnetic radiation that optically interacts with a sample to produce sample-interacted light; a first optical element that optically interacts with the sample-interacted light to generate a characteristic optical channel whose light can be utilized to determine a characteristic of the sample; a second optical element that optically interacts with the sample-interacted light or the electromagnetic radiation to thereby generate a normalization optical channel whose light has an intensity substantially equal to an intensity of the light of the characteristic optical channel; and a detector positioned to measure the intensity of the light of the characteristic optical channel and the intensity of the light of the normalization optical channel, and thereby generate a signal utilized to determine the characteristic of the sample.

2. An optical computing device as defined in paragraph 1, further comprising an electromagnetic radiation source that generates the electromagnetic radiation.

3. An optical computing device as defined in any of paragraphs 1-2, wherein the electromagnetic radiation is radiation emanating from the sample.

4. An optical computing device as defined in any of paragraphs 1-3, wherein the detector comprises a first detector positioned to receive the light of the characteristic optical channel; and a second detector positioned to receive the light of the normalization optical channel.

5. An optical computing device as defined in any of paragraphs 1-4, further comprising a signal processor communicably coupled to the detector to computationally determine the characteristic of the sample.

6. An optical computing device as defined in any of paragraphs 1-5, wherein the first optical element is at least one of a narrow band optical filter or an integrated computational element.

7. An optical computing device as defined in any of paragraphs 1-6, wherein the second optical element is at least one of a neutral density element whose transmission value is substantially equal to a transmission value of the first optical element; or an aperture whose physical dimensions are adapted to generate the light of the normalization optical channel.

8. An optical computing device as defined in any of paragraphs 1-7, wherein the second optical element comprises at least two optical elements comprised of a combination of one or more apertures and one or more neutral density elements; or a combination of one or more apertures and one or more dispersive elements.

9. An optical computing device as defined in any of paragraphs 1-8, wherein the at least two optical elements that generate the normalization optical channel are arranged in series relative to one another to thereby combinatorily generate the light of the normalized optical channel.

10. An optical computing device as defined in any of paragraphs 1-9, wherein the at least two optical elements that generate the normalization optical channel comprise at least one optical element whose transmission function derivative as a function of wavelength is substantially non-zero.

11. An optical computing device as defined in any of paragraphs 1-10, wherein the at least two optical elements that generate the normalization optical channel further comprise an optical element whose optical bandpass transmission function is substantially linear and whose slope is non-zero; and an aperture, each combined to produce the normalization optical channel whose intensity is substantially equal to the characteristic optical channel.

12. An optical computing device as defined in any of paragraphs 1-11, wherein a ratio of the light intensity of the characteristic optical channel to the light intensity of the normalization optical channel is 2:1, 1:2, 1.2:1, 1:1.2, 1.1:1, 1:1.1, less than 1.05:1, or 1:1.05.

13. An optical computing device as defined in any of paragraphs 1-12, further comprising a moveable assembly configured for rotation, wherein the first optical element and the second optical element are disposed within the moveable assembly for rotation therewith.

14. An optical computing method to determine a characteristic of a sample, the method comprising optically interacting electromagnetic radiation with a sample to produce sample-interacted light; optically interacting a first optical element with the sample-interacted light to generate a characteristic optical channel whose light can be utilized to determine a characteristic of the sample; optically interacting a second optical element with the sample-interacted light or the electromagnetic radiation to generate a normalization optical channel whose light has an intensity substantially equal to an intensity of the light of the characteristic optical channel; generating a signal corresponding to the intensity of the light of the characteristic optical channel and the intensity of the light of the normalization optical channel through utilization of a detector; and determining the characteristic of the sample using the signal.

15. An optical computing method as defined in paragraph 14, further comprising generating the electromagnetic radiation using an electromagnetic radiation source.

16. An optical computing method as defined in any of paragraphs 14 or 15, wherein the electromagnetic radiation emanates from the sample.

17. An optical computing method as defined in any of paragraphs 14-16, wherein determining the characteristic of the sample is achieved using a signal processor communicably coupled to the detector.

18. An optical computing method as defined in any of paragraphs 14-17, further comprising providing the first optical element as at least one of a narrow band optical filter or an integrated computational element.

19. An optical computing method as defined in any of paragraphs 14-18, further comprising providing the second optical element as at least one of a neutral density element whose transmission value is substantially equal to a transmission value of the first optical element; or an aperture whose physical dimensions are adapted to generate the light of the normalization optical channel.

20. An optical computing method as defined in any of paragraphs 14-19, further comprising providing the second optical element as at least two optical elements comprised of a combination of one or more apertures and one or more neutral density elements; or a combination of one or more apertures and one or more dispersive elements.

21. An optical computing method as defined in any of paragraphs 14-20, further comprising arranging at least two optical elements in series relative to one another to thereby combinatorily generate the light of the normalized optical channel.

22. An optical computing method as defined in any of paragraphs 14-21, wherein the at least two optical elements comprise at least one optical element whose transmission function derivative is a function of wavelength is substantially non-zero.

23. An optical computing method as defined in any of paragraphs 14-22, wherein the at least two optical elements further comprise an optical element whose optical bandpass transmission function is substantially linear and whose slope is non-zero; and an aperture, each combined to produce the normalization optical channel whose intensity is substantially equal to the characteristic optical channel.

24. An optical computing method as defined in any of paragraphs 14-23, wherein a ratio of the light intensity of the characteristic optical channel to the light intensity of the normalization optical channel is 2:1, 1:2, 1.2:1, 1:1.2, 1.1:1, 1:1.1, less than 1.05:1, or 1:1.05.

25. An optical computing method as defined in any of paragraphs 14-25, wherein optically interacting the first and second optical elements further comprises rotating the first and second optical elements using a moveable assembly.

Although various embodiments and methodologies have been shown and described, the invention is not limited to such embodiments and methodologies, and will be understood to include all modifications and variations as would be apparent to one ordinarily skilled in the art. Therefore, it should be understood that the invention is not intended to be limited to the particular forms disclosed. Rather, the intention is to cover all modifications, equivalents and alternatives falling within the spirit and scope of the invention as defined by the appended claims.

What is claimed is:
1. An optical computing device, comprising:
electromagnetic radiation that optically interacts with a sample to produce sample-interacted light;
a first optical element that optically interacts with the sample-interacted light to generate a characteristic optical channel whose light can be utilized to determine a characteristic of the sample;
a second optical element that optically interacts with the sample-interacted light or the electromagnetic radiation to thereby generate a normalization optical channel whose light has an intensity substantially equal to an intensity of the light of the characteristic optical channel; and a detector positioned to measure the intensity of the light of the characteristic optical channel and the intensity of the light of the normalization optical channel, and thereby generate a signal utilized to determine the characteristic of the sample.

2. The optical computing device as defined in claim 1, further comprising an electromagnetic radiation source that generates the electromagnetic radiation.

3. The optical computing device as defined in claim 1, wherein the electromagnetic radiation is radiation emanating from the sample.

4. The optical computing device as defined in claim 1, wherein the detector comprises:
   a first detector positioned to receive the light of the characteristic optical channel; and
   a second detector positioned to receive the light of the normalization optical channel.

5. The optical computing device as defined in claim 1, further comprising a signal processor communicably coupled to the detector to computationally determine the characteristic of the sample.

6. The optical computing device as defined in claim 1, wherein the first optical element is at least one of a narrow band optical filter or an integrated computational element.

7. The optical computing device as defined in claim 1, wherein the second optical element is at least one of:
   a neutral density element whose transmission value is substantially equal to a transmission value of the first optical element; or
   an aperture whose physical dimensions are adapted to generate the light of the normalization optical channel.

8. The optical computing device as defined in claim 1, wherein the second optical element comprises at least two optical elements comprised of:
   a combination of one or more apertures and one or more neutral density elements; or
   a combination of one or more apertures and one or more dispersive elements.

9. The optical computing device as defined in claim 8, wherein the at least two optical elements that generate the normalization optical channel are arranged in series relative to one another to thereby combinatorily generate the light of the normalized optical channel.

10. The optical computing device as defined in claim 8, wherein the at least two optical elements that generate the normalization optical channel comprise at least one optical element whose transmission function derivative as a function of wavelength is substantially non-zero.

11. The optical computing device as defined in claim 8, wherein the at least two optical elements that generate the normalization optical channel further comprise:
   an optical element whose optical bandpass transmission function is substantially linear and whose slope is non-zero; and
   an aperture, each combined to produce the normalization optical channel whose intensity is substantially equal to the characteristic optical channel.

12. The optical computing device as defined in claim 1, wherein a ratio of the light intensity of the characteristic optical channel to the light intensity of the normalization optical channel is 2:1, 1:2, 1.2:1, 1:1.2, 1.1:1, 1:1.1, less than 1.05:1, or 1:1.05.

13. The optical computing device as defined in claim 1, further comprising a moveable assembly configured for rotation, wherein the first optical element and the second optical element are disposed within the moveable assembly for rotation therewith.

14. An optical computing method to determine a characteristic of a sample, the method comprising:
   optically interacting electromagnetic radiation with a sample to produce sample-interacted light;
   optically interacting a first optical element with the sample-interacted light to generate a characteristic optical channel whose light can be utilized to determine a characteristic of the sample;
   optically interacting a second optical element with the sample-interacted light or the electromagnetic radiation to generate a normalization optical channel whose light has an intensity substantially equal to an intensity of the light of the characteristic optical channel;
   generating a signal corresponding to the intensity of the light of the characteristic optical channel and the intensity of the light of the normalization optical channel through utilization of a detector; and
   determining the characteristic of the sample using the signal.

15. The optical computing method as defined in claim 14, further comprising generating the electromagnetic radiation using an electromagnetic radiation source.

16. The optical computing method as defined in claim 14, wherein the electromagnetic radiation emanates from the sample.

17. The optical computing method as defined in claim 14, wherein determining the characteristic of the sample is achieved using a signal processor communicably coupled to the detector.

18. The optical computing method as defined in claim 14, further comprising providing the first optical element as at least one of a narrow band optical filter or an integrated computational element.

19. The optical computing method as defined in claim 14, further comprising providing the second optical element as at least one of:
   a neutral density element whose transmission value is substantially equal to a transmission value of the first optical element; or
   an aperture whose physical dimensions are adapted to generate the light of the normalization optical channel.

20. The optical computing method as defined in claim 14, further comprising providing the second optical element as at least two optical elements comprised of:
   a combination of one or more apertures and one or more neutral density elements; or
   a combination of one or more apertures and one or more dispersive elements.

21. The optical computing method as defined in claim 20, further comprising arranging at least two optical elements in series relative to one another to thereby combinatorily generate the light of the normalized optical channel.

22. The optical computing method as defined in claim 20, wherein the at least two optical elements comprise at least one optical element whose transmission function derivative is a function of wavelength is substantially non-zero.

23. The optical computing method as defined in claim 20, wherein the at least two optical elements further comprise:
   an optical element whose optical bandpass transmission function is substantially linear and whose slope is non-zero; and
   an aperture, each combined to produce the normalization optical channel whose intensity is substantially equal to the characteristic optical channel.

24. The optical computing method as defined in claim 14, wherein a ratio of the light intensity of the characteristic optical channel to the light intensity of the normalization optical channel is 2:1, 1:2, 1.2:1, 1:1.2, 1.1:1, 1:1.1, less than 1.05:1, or 1:1.05.

25. The optical computing method as defined in claim 14, wherein optically interacting the first and second optical elements further comprises rotating the first and second optical elements using a moveable assembly.

* * * * *